US00PP26460P2

(12) United States Plant Patent

Kuang-Liang

(10) Patent No.: US PP26,460 P2

(45) Date of Patent: Mar. 8, 2016

(54) *POLIANTHES* PLANT NAMED 'CHIA NONG PINK SAPPHIRE'

(50) Latin Name: *Polianthes hybrida*
Varietal Denomination: Chia Nong Pink Sapphire

(71) Applicant: Huang Kuang-Liang, Chiayi (TW)

(72) Inventor: Huang Kuang-Liang, Chiayi (TW)

(73) Assignee: Berbee Beheer B.V., Lisse (NL)

( * ) Notice: Subject to any disclaimer, the term of this patent is extended or adjusted under 35 U.S.C. 154(b) by 177 days.

(21) Appl. No.: 13/999,246

(22) Filed: Jan. 31, 2014

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — C. A. Whealy

(57) ABSTRACT

A new and distinct cultivar of *Polianthes* plant named 'Chia Nong Pink Sapphire', characterized by its upright plant habit; numerous double-type flowers that are light lilac pink in color; flowers arranged on upright and strong flower scapes; pleasant fragrance; and good garden performance.

2 Drawing Sheets

Botanical designation: *Polianthes hybrida.*

Cultivar denomination: 'CHIA NONG PINK SAPPHIRE'.

BACKGROUND OF THE INVENTION

The present invention relates to a new and distinct cultivar of *Polianthes* plant, botanically known as *Polianthes hybrida* and hereinafter referred to by the name 'Chia Nong Pink Sapphire'.

The new *Polianthes* plant originated from a cross-pollination made by the Inventor in 1997 in Chiayl City, Taiwan of a proprietary selection of *Polianthes tuberosa*×*Polianthes howardii* identified as code number 77-A-05, not patented, as the female, or seed, parent with *Polianthes tuberosa* 'Double', not patented, as the male, or pollen, parent. The new *Polianthes* plant was discovered and selected by the Inventor as a single flowering plant within the progeny of the stated cross-pollination in a controlled greenhouse environment in Chiayl City, Taiwan in 1997.

Asexual reproduction of the new *Polianthes* plant by divisions in a controlled environment in Puli, Taiwan since 2010 has shown that the unique features of this new *Polianthes* plant are stable and reproduced true to type in successive generations.

SUMMARY OF THE INVENTION

Plants of the new *Polianthes* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Chia Nong Pink Sapphire'. These characteristics in combination distinguish 'Chia Nong Pink Sapphire' as a new and distinct *Polianthes* plant:

1. Upright plant habit.
2. Numerous double-type flowers that are light lilac pink in color.
3. Flowers arranged on upright and strong flower scapes.
4. Pleasant fragrance.
5. Good garden performance.

Plants of the new *Polianthes* differ primarily from plants of the female parent selection in the following characteristics:

1. Plants of the new *Polianthes* have double flowers whereas plants of the female parent selection have single flowers.
2. Plants of the new *Polianthes* have larger flowers than plants of the female parent selection.
3. Plants of the new *Polianthes* and the female parent selection differ in flower color as plants of the female parent selection have pink-colored flowers.

Plants of the new *Polianthes* differ primarily from plants of the male parent, 'Double', in the following characteristics:

1. Inflorescences of plants of the new *Polianthes* are more compact than inflorescences of plants of 'Double'.
2. Plants of the new *Polianthes* and 'Double' differ in flower color as plants of 'Double' have white-colored flowers.

Plants of the new *Polianthes* can be compared to plants of *Polianthes tuberosa* 'The Pearl', not patented. In side-by-side comparisons, plants of the new *Polianthes* and 'The Pearl' differed in the following characteristics:

1. Plants of the new *Polianthes* were taller than plants of 'The Pearl'.
2. Leaves of plants of the new *Polianthes* were longer than leaves of 'The Pearl'.
3. Plants of the new *Polianthes* had longer inflorescences with more flowers per inflorescence than plants of 'The Pearl'.
4. Plants of the new *Polianthes* and 'The Pearl' differed in flower color as plants of 'The Pearl' had white-colored flowers.

BRIEF DESCRIPTION OF THE PHOTOGRAPHS

The accompanying colored photographs illustrate the overall appearance of the new *Polianthes* plant showing the colors as true as it is reasonably possible to obtain in colored reproductions of this type. Colors in the photographs may differ slightly from the color values cited in the detailed botanical description which accurately describe the colors of the new *Polianthes* plant.

The photograph on the first sheet comprises a side perspective view of a typical flowering plant of 'Chia Nong Pink Sapphire' grown in a container.

The photograph on the second sheet is a close-up view of a typical inflorescence of 'Chia Nong Pink Sapphire'.

DETAILED BOTANICAL DESCRIPTION

The aforementioned photographs and following observations, measurements and values describe plants grown during the late summer in ground beds and containers in a glass-covered greenhouse in Lisse, The Netherlands and under cultural practices typical of commercial *Polianthes* production. During the production of the plants, day temperatures ranged from 12° C. to 32° C. and night temperatures ranged from 3° C. to 18° C. Plants were one year old when the photographs and description were taken. In the following description, color references are made to The Royal Horticultural Society Colour Chart, 2007 Edition, except where general terms of ordinary dictionary significance are used.

Botanical classification: *Polianthes hybrida* 'Chia Nong Pink Sapphire'.

Parentage:

*Female, or seed, parent*.—Proprietary selection of *Polianthes tuberosa*×*Polianthes howardii* identified as code number 77-A-05, not patented.

*Male, or pollen, parent*.—Polianthes tuberosa 'Double', not patented.

Propagation:

*Type*.—By tissue culture.

*Time to initiate roots, summer*.—About two weeks at soil temperatures about 20° C.

*Time to produce a rooted plant, summer*.—About 25 days at soil temperatures about 20° C.

*Root description*.—Medium in thickness, fleshy; grey in color.

*Rooting habit*.—Moderate branching; medium density.

*Rhizomes*.—Length: About 4.2 cm. Diameter: About 2.8 cm. Shape: Ovate. Texture: Smooth, glabrous. Color: Close to N199C and 200C.

Plant description:

*Plant form and growth habit*.—Herbaceous flowering perennial plant; upright plant habit with strong upright flower scapes; leaves and flowering stems basal with leaves along the flower scapes; moderately vigorous to vigorous growth habit.

*Plant height*.—About 102.7 cm.

*Plant width* (*spread*).—About 44.2 cm.

Leaf description:

*Arrangement and appearance*.—Leaves arranged in a basal rosette and along flower scape; leaves simple and sessile.

*Leaf length, rosette leaves*.—About 35.8 cm.

*Leaf width, rosette leaves*.—About 2.4 cm.

*Leaf length, flower scape leaves*.—About 16.5 cm.

*Leaf width, flowering scape leaves*.—About 2.1 cm.

*Shape*.—Ligulate.

*Apex*.—Long acuminate.

*Base*.—Cuneate, decurrent.

*Margin*.—Entire.

*Texture, upper and lower surfaces*.—Smooth, glabrous.

*Venation pattern*.—Parallel.

*Color*.—Developing leaves, upper surface: Close to 143C. Developing leaves, lower surface: Close to between 143C and 146B. Fully expanded leaves, upper surface: Close to 143B; venation, close to 137B. Fully expanded leaves, lower surface: Close to 143C; main vein, close to 144B; secondary veins, close to 137B to 137C.

Flower description:

*Flower type and flowering habit*.—Double-type flowers arranged in terminal racemes supported on strong upright scapes; flowers face upright to slightly outwardly; freely flowering habit with about 46 flowers developing per inflorescence.

*Fragrance*.—Strongly fragrant; pleasant and sweet.

*Natural flowering season*.—Plants begin flowering about four months after planting; flowering continuous from early August into September in The Netherlands.

*Postproduction longevity*.—Flowers last about one week the plant; flowers not persistent.

*Flower buds*.—Height: About 5.1 cm. Diameter: About 1.2 cm. Shape: Oblong to oblanceolate. Color: Close to 75C to 75D; towards the apex, tinged with close to 148C; towards the base, close to 145A.

*Inflorescence height*.—About 46.2 cm.

*Inflorescence diameter*.—About 10.3 cm.

*Flower diameter*.—About 6 cm.

*Flower depth*.—About 5.1 cm.

*Perianth*.—Quantity and arrangement: Typically six outer segments arranged in two whorls and about 18 inner segments arranged in three whorls; lower 20% of the segments are fused into a narrow tube; upper free part of segments flaring outwardly. Outer segment length: About 5.4 cm. Outer segment width: About 1 cm. Outer segment lobe shape: Oblanceolate. Outer segment apex: Acute. Outer segment margin: Entire. Outer segment texture, upper and lower surfaces: Smooth, glabrous; somewhat velvety. Outer segment color: When opening, upper surface: Close to 69D heavily dotted with close to 70B; towards the base, close to 145A. When opening, lower surface: Close to 75D slightly dotted with close to 70A; apex tinged with close to 153D; towards the base, close to 145A. Fully opened, upper surface: Close to 69D heavily dotted with close to 70B; white axial central band, close to 155C; towards the base, close to 145A. Fully opened, lower surface: Close to 159D moderately dotted with close to 63B; apex tinged with close to 153D; towards the base, close to 145A. Inner segment length: About 5 cm. Inner segment width: About 9 mm. Inner segment lobe shape: Oblanceolate. Inner segment apex: Acute. Inner segment margin: Entire. Inner segment texture, upper and lower surfaces: Smooth, glabrous; somewhat velvety. Inner segment color: When opening, upper and lower surfaces: Close to 69C to 69D. Fully opened, upper and lower surfaces: Close to 69D heavily dotted with close to 70B; towards the base, close to 145A.

*Peduncles* (*flower scapes*).—Length: About 93.8 cm. Diameter: About 7.5 mm. Aspect: Upright. Strength: Strong. Texture: Smooth, glabrous. Color: Close to 143B covered with thin waxy layer, close to 138B.

*Pedicels*.—Length: About 1 cm. Diameter: About 3 mm. Aspect: About 30° from peduncle axis. Strength: Strong. Texture: Smooth, glabrous. Color: Close to 145B.

*Flower bracts*.—Arrangement: One at the base of the pedicel. Length: About 3.5 cm. Width: About 1.3 cm. Shape: Narrowly deltoid. Apex: Narrowly acute. Base: Cuneate. Margin: Entire. Texture, upper and lower surfaces: Smooth, glabrous. Color, upper and lower surfaces: Close to 145C; towards the margins, close to 144C.

*Reproductive organs*.—Stamens: Quantity per flower: Typically none or one. Filament length: About 1.3 cm. Filament color: Close to 69D and NN155C. Anther shape: Narrowly oblong; dorsifixed. Anther length: About 0.5 mm. Anther color: Close to 150D. Pollen amount: Scarce to moderate. Pollen color: Close to 4A. Pistils: Quantity per flower: None or one. Pistil length: About 1.5 cm. Style length: About 1.4 cm. Style color: Close to NN155C to NN155D. Stigma shape: Clavate. Stigma color: Close to NN155C to NN155D. Ovary color: Close to 1458.

*Seeds and fruits*.—Seed and fruit development have not been observed on plants of the new *Polianthes*.

Disease & pest resistance: Plants of the new *Polianthes* have not been noted to be resistant to pathogens and pests common to *Polianthes* plants.

Garden performance: Plants of the new *Polianthes* have been observed to have good garden performance and to tolerate rain, wind, high temperatures about 32° C. and to be hardy to USDA Hardiness Zone 8b.

It is claimed:

1. A new and distinct *Polianthes* plant named 'Chia Nong Pink Sapphire' as illustrated and described.

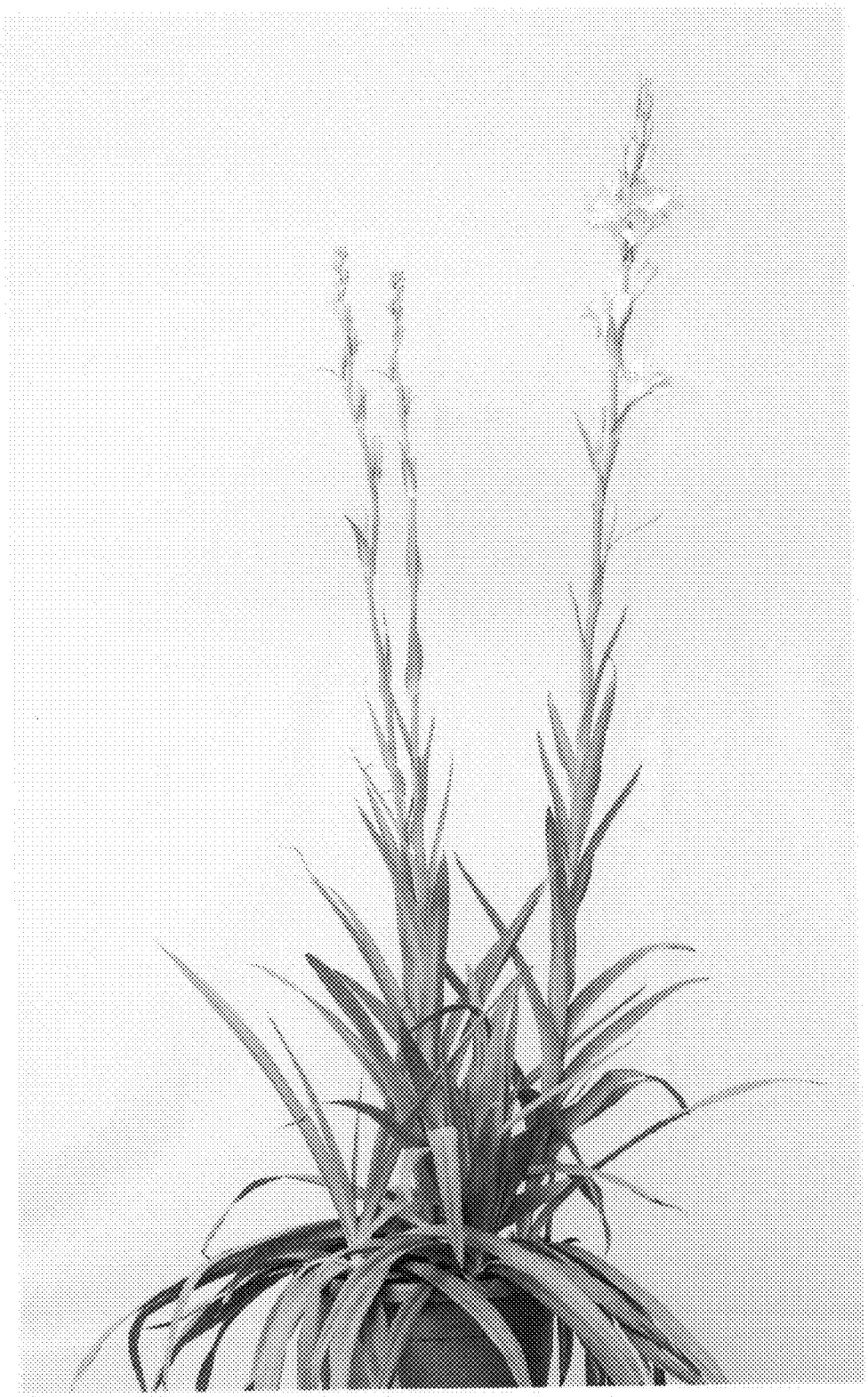

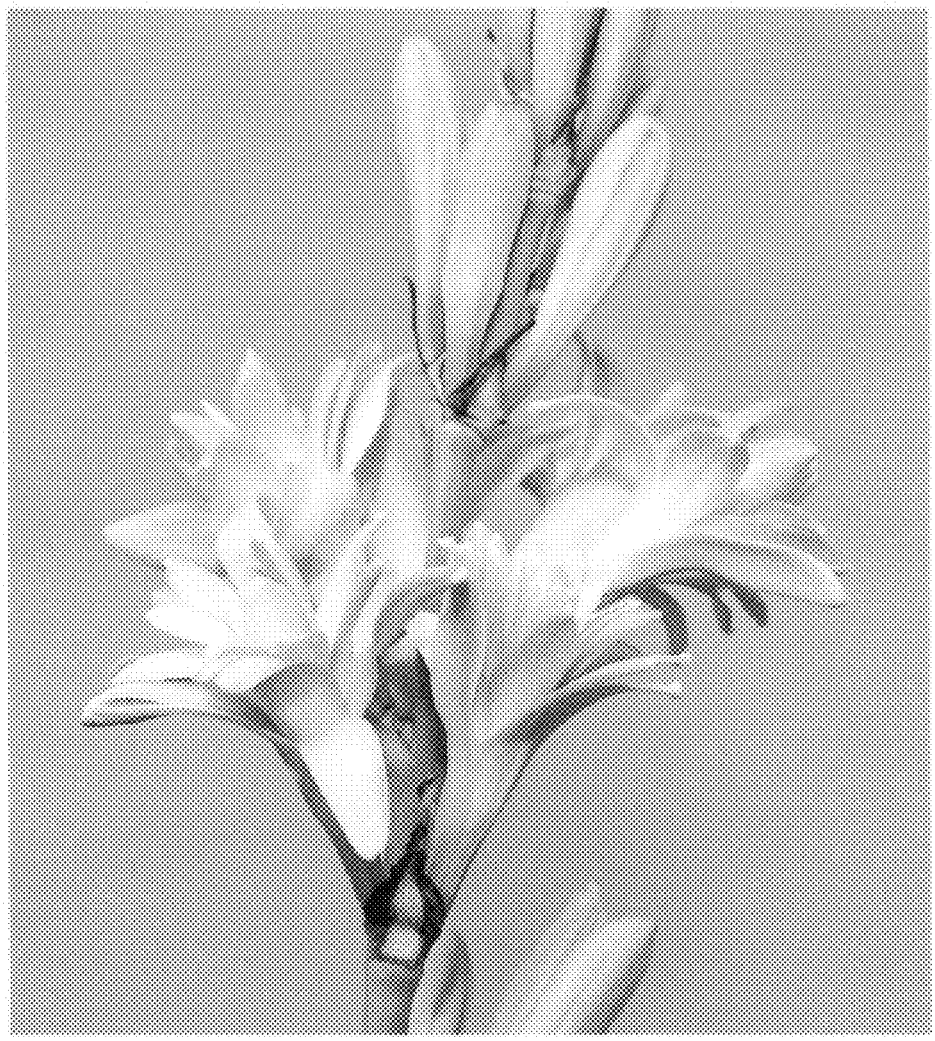

* * * * *